US008243272B2

(12) United States Patent
Adams (10) Patent No.: US 8,243,272 B2
(45) Date of Patent: Aug. 14, 2012

(54) SYSTEMS AND METHODS FOR DETECTING NORMAL LEVELS OF BACTERIA IN WATER USING A MULTIPLE ANGLE LIGHT SCATTERING (MALS) INSTRUMENT

(75) Inventor: John A. Adams, Escondido, CA (US)

(73) Assignee: JMAR LLC, San Diego, CA (US)

( * ) Notice: Subject to any disclaimer, the term of this patent is extended or adjusted under 35 U.S.C. 154(b) by 248 days.

(21) Appl. No.: 12/868,654

(22) Filed: Aug. 25, 2010

(65) Prior Publication Data
US 2011/0066382 A1 Mar. 17, 2011

Related U.S. Application Data

(63) Continuation-in-part of application No. 12/483,203, filed on Jun. 11, 2009, now Pat. No. 8,134,704, which is a continuation of application No. 11/564,773, filed on Nov. 29, 2006, now Pat. No. 7,551,279, which is a continuation-in-part of application No. 11/539,166, filed on Oct. 5, 2006, now Pat. No. 7,554,661, which is a continuation-in-part of application No. 11/381,346, filed on May 2, 2006, now Pat. No. 7,564,551, which is a continuation-in-part of application No. 11/231,350, filed on Sep. 19, 2005, now Pat. No. 7,532,327.

(51) Int. Cl.
*G01N 21/00* (2006.01)
(52) U.S. Cl. ......... 356/338; 356/335; 356/336; 356/337
(58) Field of Classification Search ........... 356/335–343
See application file for complete search history.

(56) References Cited

U.S. PATENT DOCUMENTS
4,273,443 A 6/1981 Hogg
(Continued)

FOREIGN PATENT DOCUMENTS
WO 2009093017 A1 7/2009

OTHER PUBLICATIONS

Extended European Search Report and Opinion issued by the European Patent Office for EP 06784381.3 on Jun. 6, 2011 (7 pages).
International Search Report issued for corresponding International Application PCT/US2011/049236 on Mar. 28, 2012 (5 pages).

*Primary Examiner* — Michael P Stafira
(74) *Attorney, Agent, or Firm* — Procopio Cory Hargreaves & Savitch LLP; Noel C. Gillespie (57) ABSTRACT

A particle detection system uses a camera to produce a picture based on the scattered light generated by a particle in a liquid medium, when a laser beam is incident on the particle. These pictures are then automatically analyzed through the use of a processing system (e.g., a computer). The processing system is configured to record the forward scattering intensity (e.g., amplitude) and the picture of the scattered light rays to generate a classification of the particle causing the scattering. Count rate and trends of the classified particles are monitored to detect a change that is representative of the overall health safety of the water or by knowing the levels of bacteria in process water, such as Reverse Osmosis (RO) feed water, reject brine, and product water, the operator may better monitor the life and condition of the RO membrane.

27 Claims, 11 Drawing Sheets

U.S. PATENT DOCUMENTS

| | | |
|---|---|---|
| 4,523,841 A | 6/1985 | Brunsting et al. |
| 5,434,667 A * | 7/1995 | Hutchins et al. ............. 356/338 |
| 7,390,662 B2 * | 6/2008 | Riley et al. ..................... 436/10 |
| 2007/0269897 A1 | 11/2007 | Tanaka et al. |
| 2008/0172185 A1 | 7/2008 | Yi et al. |
| 2009/0316138 A1 | 12/2009 | Herzog |
| 2010/0007505 A1 | 1/2010 | Adams et al. |
| 2010/0108910 A1 | 5/2010 | Morrell et al. |

* cited by examiner

FIG. 4
E. coli

FIG. 2C
8 micron sphere

FIG. 3C
Giardia

FIG. 2A 2 micron sphere  FIG. 2B 4 micron sphere

FIG. 3B
Inorganic "dirt"

FIG. 3A
Crypto

SYSTEMS AND METHODS FOR DETECTING NORMAL LEVELS OF BACTERIA IN WATER USING A MULTIPLE ANGLE LIGHT SCATTERING (MALS) INSTRUMENT

FIELD OF THE INVENTION

This application claims the priority as a Continuation-in-Part under 35 U.S.C. 120 to U.S. patent application Ser. No. 12/483,203, entitled "Systems and Methods For Detecting Normal Levels of Bacteria in Water Using a Multiple Angle Light Scattering (MALS) Instrument," filed Jun. 11, 2009, which in turn is a Continuation under 35 U.S.C. 120 to U.S. patent application Ser. No. 11/564,733, entitled "Systems and Methods For Detecting Normal Levels of Bacteria in Water Using a Multiple Angle Light Scattering (MALS) Instrument," filed Nov. 29, 2006, which is in turn a Continuation-In-Part (CIP) under 35 U.S.C. 120 to U.S. patent application Ser. No. 11/539,166, entitled "Systems and Methods For Detection and Classification of Waterborne Particles Using a Multiple Angle Light Scattering (MALS) Instrument," filed Oct. 5, 2006, which is in turn a CIP of U.S. patent application Ser. No. 11/381,346 entitled "Systems and Methods For a High Capture Angle, Multiple Angle Light Scattering (MALS) Instrument," filed May 2, 2006, which is in turn a CIP of U.S. patent application Ser. No. 11/231,350, entitled "Systems and Methods For Detecting Scattered Light From a Particle Using Illumination Incident at an Angle," filed Sep. 19, 2005, all of which are incorporated herein by reference as if set forth in full.

BACKGROUND

1. Field of the Invention

Embodiments described herein relate to detecting and classifying particles in a liquid using multi-angle-light-scattering (MALS), and in particular to monitoring of water for normal concentration levels of bacteria, including Heterotrophic Plate Count (HPC) bacteria, that are found in water for human consumption.

2. Background of the Invention

A major concern for municipal and commercial water treatment facilities is the detection and control of pathogenic microorganisms, both known and emerging, in potable water treatment and distribution. In addition, there may exist levels of Heterotrophic Plate Count (HPC) bacteria that must not be allowed to exceed standards. In addition, there are not only a number of chlorine resistant pathogens such as *Cryptosporidium* that can contaminate drinking water systems, but also potentially harmful microorganisms that can be introduced, either accidentally or intentionally, and propagate under suitable environmental conditions. Due to the length of time for standard laboratory methods to yield results, typically 24-72 hours, there has not been a reliable system to detect microbial levels in real-time and on-line to provide the water system operator with timely information on bacterial levels present in the water. Because of these expanding challenges, there has been an accelerated development of rapid tests and real-time methods to address the pressing needs of the water treatment community.

Conventional microbiological methods can be used to detect some of the microorganisms; however, such methods provide limited results. Analytical methods in microbiology were developed over 120 years ago and are very similar today. These methods incorporate the following steps: sampling, culturing and isolating the microbes in a suitable growth media by incubation, identifying the organisms through microscopic examination or stains, and quantifying the organisms. *Cryptosporidium* and *Giardia* form oocysts or cysts and cannot easily be cultured in conventional ways. To detect these protozoan pathogens, an amount of water containing suspected pathogens, typically 10 liters, is sent through a special filter to collect and concentrate the organisms. Then the filter is eluted and the organisms further processed by staining the organisms and sending the concentrated solution through flow cytometry for example. These procedures, which can be found in Standard Methods or ASME, require ascetic technique in sampling and handling, skilled technicians to perform the analysis, and a number of reagents, materials, and instruments to obtain results. Practically, such methods have proved to be time consuming, costly, and of little effectiveness for many current environmental field applications.

In order to reduce the amount of time to access microbiological results, a number of methods have been developed, mostly in the field of medicine. These faster tests have been improved and adapted to the environmental field and are generally categorized as 1) accelerated and automated tests 2) rapid tests and 3) contamination warning systems (CWS).

Accelerated tests are by grab sample and results can be obtained in 4 hours to 18 hours. Accelerated tests include immunoassays, ATP luminescence, and fluorescent antibody fixation. Rapid tests are also by grab sample and require manipulation of the sample to 'tag' the microbes with an identifiable marker or concentrate the microbe's genetic material (DNA) for subsequent identification. Results are normally available in 1-3 hours. These types of tests include Polymerase Chain Reaction (PCR) and Flow Cytometry.

Real time bacterial monitoring systems are continuous devices that detect levels of bacteria within a few minutes and may include laser based multi-angle light scattering (MALS) or multi-parameter chemical & particle instruments that detect water quality changes inferring potential biological changes. Continuous, real time detection of pathogens in water surveillance was first tried in the late 1960's and has progressed through a series of development steps until the first public field demonstration in 2002.

When light strikes a particle a characteristic scattering pattern is emitted. The scattering pattern encompasses many features of the particle including the size, shape, internal structures (morphology), particle surface, and material composition. Each type of microorganism will scatter light giving off a unique pattern herein called a Bio-Optical Signature. In traditional MALS, photo-detectors collect the scattered light and capture the patterns, which are then sent to a computer for analysis.

In addition to detecting both pathogenic and HPC bacteria in the water that occur naturally or are introduced intentionally, it is desirable to also monitor for the presence of blooms of bacteria, or biofilm slough-off, which are short-term events that normally are not caught by the grab-sample methods.

Presently, a detection system capable of meeting all of the 'ideal detection system' parameters, e.g., as cited by the American Water Works Association does not exist. Conventional devices and methods often differ in the amount of time to obtain results, degree of specificity, sampling frequency, concentration sensitivity, operating complexity, and cost of ownership.

SUMMARY

A particle classification system uses a camera to produce a picture based on the scattered light generated by a particle in a liquid medium, when a laser beam is incident on the particle.

These pictures are then automatically analyzed through the use of a processing system (e.g., a computer). The processing system is configured to record the forward scattering intensity (e.g., amplitude) and the picture of the scattered light rays to generate a classification of the particle causing the scattering.

When the particles transit the laser beam, light is scattered in all directions and is described by MIE scattering theory for particles about the size of the wavelength of light or larger. Rayleigh scattering is used when the particles are much smaller than the wavelength of light. The system calculates the quantity per unit time, or classified particle count rate, of the detected organisms, to determine whether the organisms are increasing, decreasing, or are relatively constant. This calculation allows the water system operator to gauge the overall health safety of the water. In addition, by knowing the levels of bacteria in process water, such as Reverse Osmosis (RO), feed water, reject brine, and product water, the operator may better monitor the life and condition of the RO membrane.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which.

DETAILED DESCRIPTION

In the following description, all numbers disclosed herein are approximate values, regardless whether the word "about" or "approximately" is used in connection therewith. They may vary by up to 1%, 2%, 5%, or sometimes 10 to 20%. Whenever a numerical range with a lower limit, $R_L$, and an upper limit $R_u$, is disclosed, any number R falling within the range is specifically and expressly disclosed. In particular, the following numbers R within the range are specifically disclosed: $R=R_L+k*(R_u-R_L)$, wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two numbers, R, as defined in the above is also specifically disclosed. It is also emphasized that in accordance with standard practice, various features may not be drawn to scale. In fact, the dimensions of the various features may be arbitrarily increased or reduced for clarity of discussion.

Certain embodiments described herein provide a method for real-time particle detection that uses advancements in computing power, special optics, photonics engineering, and advanced signal processing in order to provide a MALS detection system that provides simplicity, cost effectiveness, speed, and reliability. The systems described in the embodiments below are analytical systems using MALS where a side stream from a water source flows through a flow cell generally constructed from an opaque material such as corrosion-resistant metal and includes a transparent window. A laser directs a beam of light into the flow cell through the transparent window and through the water stream. In certain embodiments, the water is first characterized for background interferences to distinguish foreign particles from the pathogens' signatures resulting in a custom detection library in each particular installation.

In operation, particles pass through the beam, the scattered light is emitted and captured by a camera, converted to a digital signal, and finally sent to a processing system for analysis. The processing system is configured to record the forward scattering intensity (e.g., amplitude) and the picture of the scattered light rays.

The forward scattering amplitude and picture information form a Bio-Optical Signature or BioSignature that can be stored and processed. In an embodiment, e.g., analysis software resident in the processing system then classifies each particle into one of four classifications based upon the size and shape of the particle, as determined from the picture and forward scattering amplitude information, or BioSignature. When a BioSignature is recognized by the software, the organisms are classified within minutes. The data can be transmitted to a user screen and remote communications equipment. In certain embodiments, upon reaching a pre-set threshold level, an 'alert' can be generated and an instantaneous sample can be automatically extracted for further identification and confirmation.

Water, or other liquids for that matter, can be monitored continuously as it passes through the flow cell at a defined rate. This provides a much higher probability of detecting and classifying microorganisms compared to intermittent grab samples. The speed and performance can be further enhanced when the 1) microbial concentration level is high, 2) the water, or liquid, is of high 'clarity' or purity, 3) microorganisms have a high correlation to defined BioSignatures, and 4) the particles are of larger size, e.g., >1 micron, giving distinct scattering patterns.

In certain embodiments, if an organism is unclassified (e.g., there is not a sufficient correlation to one of the four classifications), the system can categorize it as an 'unknown' and still provide an 'alert' if a certain threshold level is reached.

Thus, the systems and methods described below can provide valuable early warnings of potential microbial contamination. The system described can be implemented economically and with extremely low operating costs. Further, the systems described do not use reagents or require costly consumables and can be compact, rugged, and easy to use, while requiring minimal operator training or expertise. In certain embodiments, 'warning' and 'alert' levels can be adjusted according to the requirements of a particular implementation and can interface with a number of communication protocols to provide immediate information for quality control or security personnel. In other embodiments, the normal levels of bacteria in the water are used to monitor for possible biofilm slough-off or gradual growth of bio-film, thus allowing the water operator to know the general quality of the water system treatment. In yet another embodiment, the normal levels of bacteria may be used to monitor the biofilm growth in water processes using Reverse Osmosis Membranes, or RO membranes. The RO membranes can become clogged or even damaged as biofilms form within the membrane structures. By monitoring the levels of bacteria that are present in the brine reject, or in the RO feed water, or in the RO output water, the embodiments described herein allow the water operator to take corrective action before the damage can occur or before product that is produced with the RO output water can be contaminated.

Figure 1A:
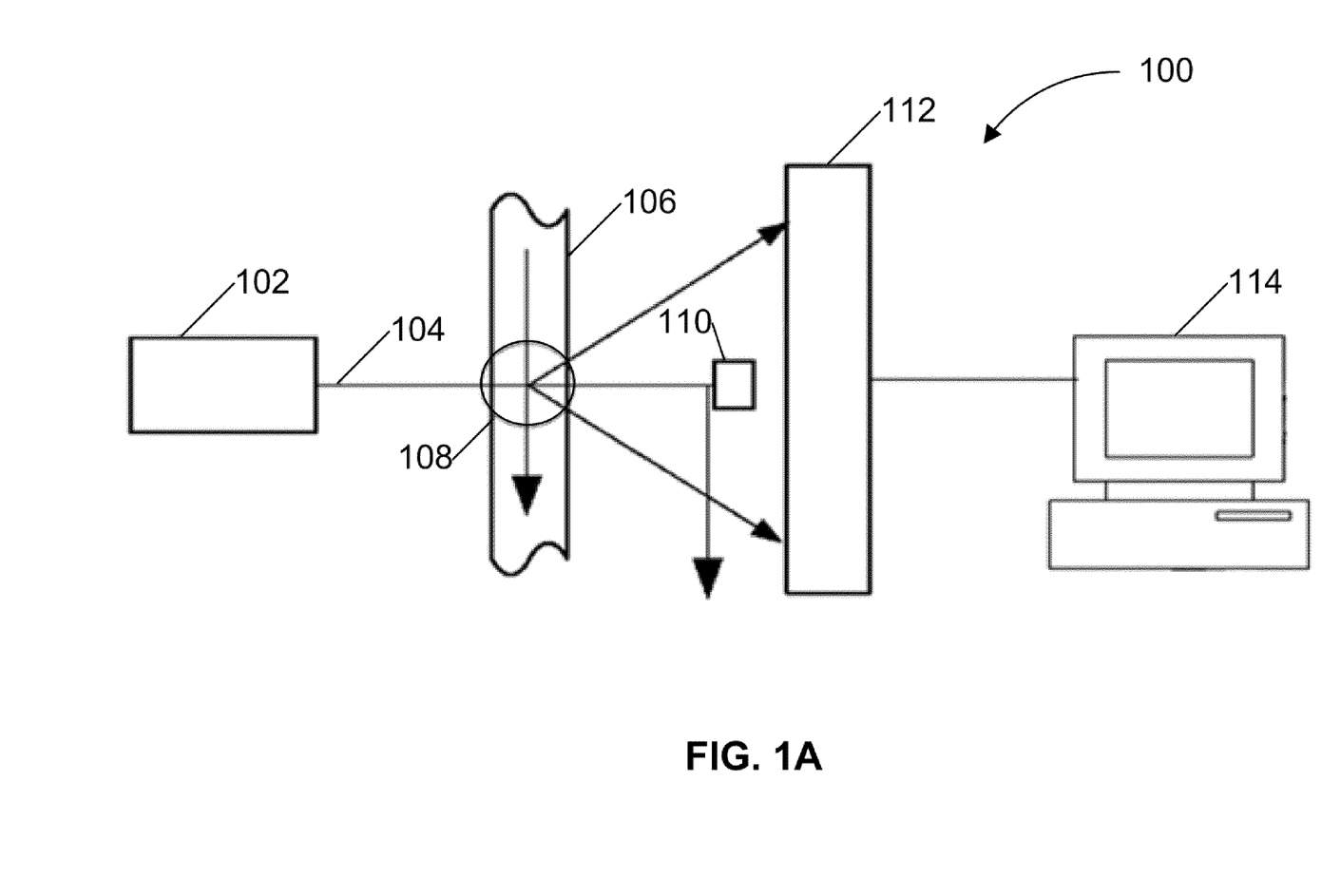
FIG. 1A is a diagram illustrating an example embodiment of a particle detection system.

FIG. 1A is a diagram illustrating an example particle detection system configured in accordance with one embodiment of the systems and methods described herein. Many of the embodiments described below are used for detecting microorganism such as *Cryptosporidium* and *Giardia*; however, it will be understood that the systems and methods described herein can be used to detect any particle capable of detection using the systems and methods described, such as bacteria and yeasts. Bacteria are typically smaller than *Cryptosporidium* and *Giardia* ranging from 500 nanometers diameter upwards to 2 microns and from oval to rod shape. Yeasts are typically the size of *Giardia* or larger. Further, while the embodiments described below generally describe detected particles in water, it will be understood that the systems and methods described can be used to detect particles in other liquids, and even in other media such as air.

System 100 comprises a light source 102 configured to provide illumination 104 to a target area 108. In the embodiment of FIG. 1A, target area 108 is within a fluid cell 106. Water intended to be interrogated for various particles, or microorganisms can flow through flow cell 106, e.g., in a downward direction as indicated. Illumination 104 will encounter particles in target zone 108, which will cause the illumination to scatter in a manner different than the illumination transmitted through the surrounding fluid medium.

Light source 102 can be configured to deliver a structured light pattern, or illumination. Thus, light source 102 can be, e.g., a coherent light source, such as a laser. Depending on the embodiment, light source 102 can comprise a single light source, such as a single laser, or a plurality of light sources, such as a plurality of lasers. Further, the wavelength of the light source can be at a fixed wavelength. Alternatively, when multiple light sources are used, the light sources can have several discrete wavelengths.

Accordingly, light source 102 can be a laser configured to produce a laser beam 104. When laser beam 104 strikes a particle within target area 108, the particle will cause the beam to scatter in a pattern that is different than the pattern produced due to beam 104 traveling through the water flowing in flow cell 106. The particles scatter beam 104 and the scattered beams are then directly incident on a camera 112.

Particles within target zone 108 will cause light from laser beam 104 to scatter as illustrated in FIG. 1A. Light scattering from target zone 108 at an angle greater than $\theta$ from the optical axis of beam 104 will be internally reflected within flow cell 106 at the interface of flow cell 106 with the external atmosphere.

Light passing through target zone 108 along the optical axis of beam 104 will generally be of a much greater intensity than that of the scattered light beams. The intensity of the beam along the optical axis can be so great that it can essentially prevent, or degrade detection of the scattered light beams. Accordingly, a beam stop 110 can be included in order to deflect beam 104 and prevent it from impinging on, and potentially saturating the camera 112.

Camera 112 then produces a picture based on the incident scattered light rays and provides the picture to a processing system 114. The processing system 114 is configured to record the forward scattering intensity (e.g., amplitude) and the picture of the scattered light rays. The forward scattering amplitude and picture information form a Bio-Optical Signature or BioSignature that can be stored and processed. The processing system 114 then classifies each particle into one of, e.g., four classifications based upon the size and shape of the particle, as determined from the picture and a degree of correlation to a stored picture, or BioSignature.

Further, system 100 can include multiple lens optics, with spatial filters, to delivered the scattered light from the particle in the target zone with less optical noise.

Figure 1B:
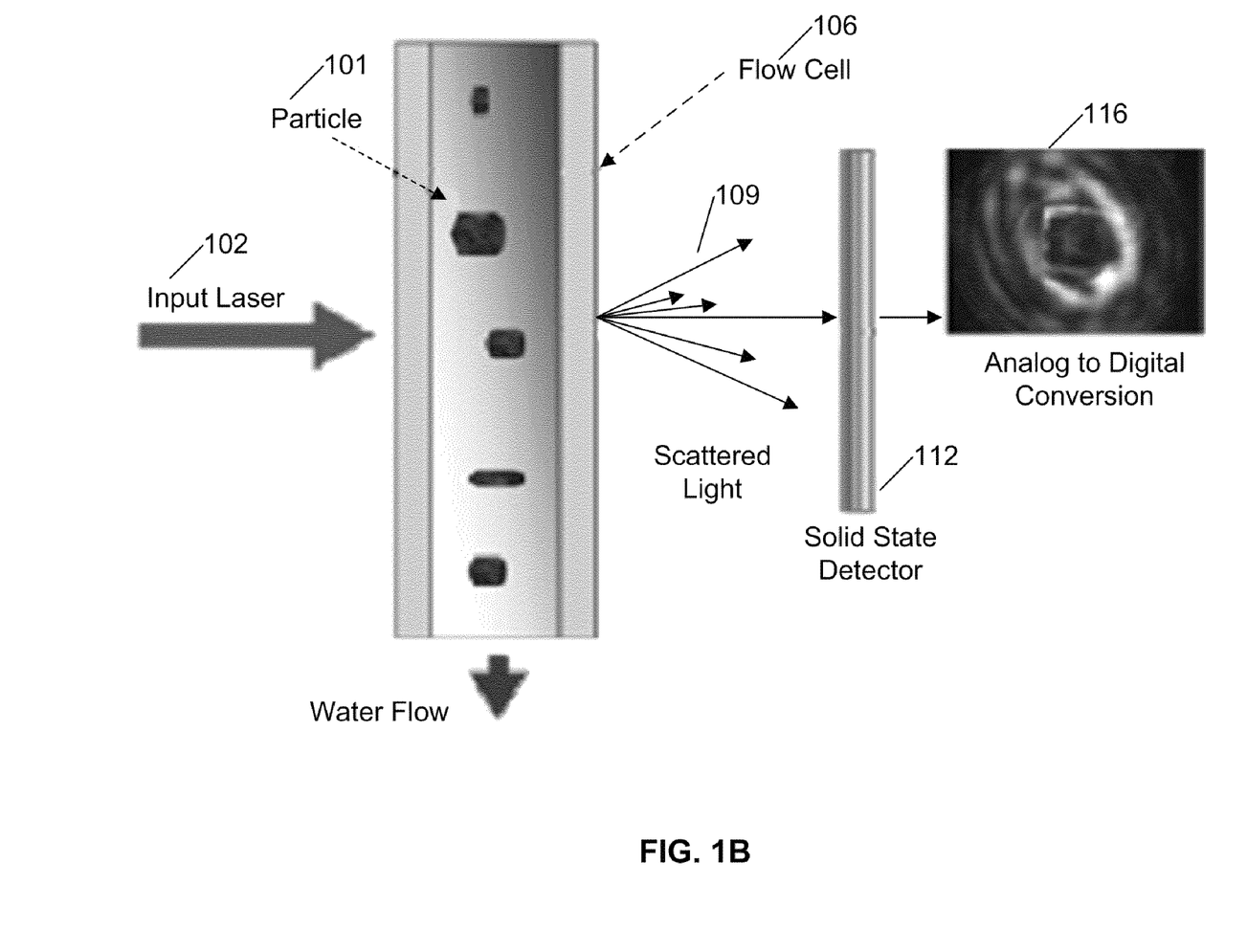
FIG. 1B is an animated image illustrating an example embodiment of a particle detection system.

FIG. 1B is an animated image illustrating an example particle detection system configured in accordance with one embodiment of the systems and methods described herein. As shown in FIG. 1B, fluid having particles 101 therein flows through flow cell 106. Light source or laser 102 illuminates the particles 101, causing light beams to scatter 109. A solid state detector or camera 112 then records an image 116 (e.g., takes or produces a picture) of the particle 101.

Figure 2A:
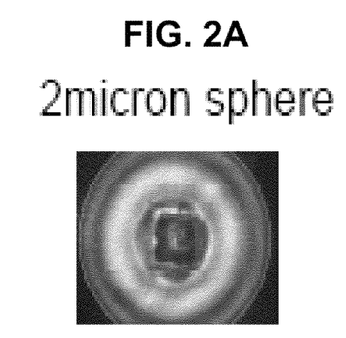
FIGS. 2A, 2B and 2C show representative images from a 2, 4, and 8 micron diameter polystyrene spheres, respectively, obtained using a particle detection system in accordance with one embodiment.
Figure 2B:
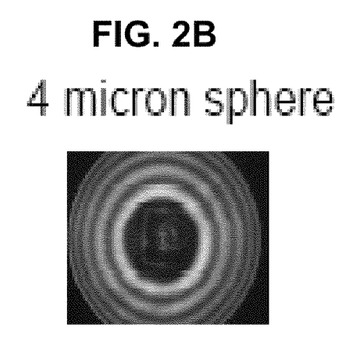
Figure 2C:
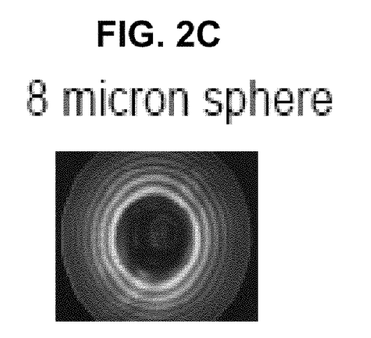
Figure 3A:
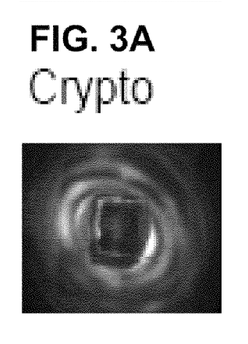
FIGS. 3A, 3B and 3C show representative images from *Cryptosporidium*, dirt, and *Giardia*, respectively obtained using a particle detection system in accordance with one embodiment.
Figure 3B:
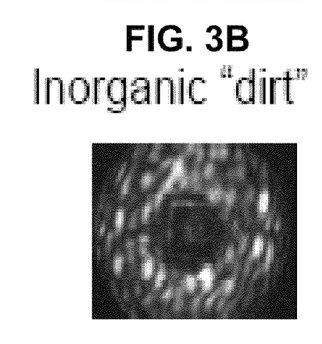
Figure 3C:
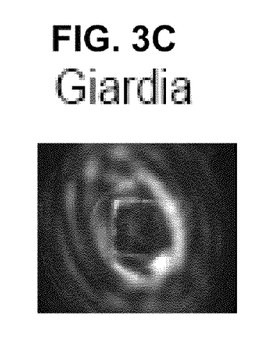
Figure 4:
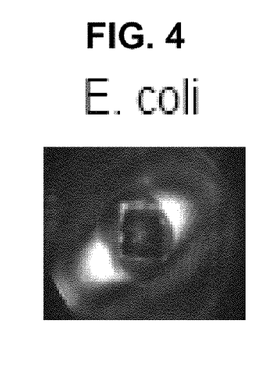
FIG. 4 shows a representative image from *E. coli* obtained using a particle detection system in accordance with one embodiment.

Each of FIGS. 2 and 3 illustrate example Bio-Optical Signatures for three different classifications for particles. FIG. 4 illustrates another Bio-Optical Signature. If, e.g., a detected particle does is not classified into one of the three classifications shown in FIGS. 2 and 3, the particle is classified in a fourth classification as "unknown".

For example, FIG. 2A is a picture illustrating a 2-micron sphere, FIG. 2B is a picture illustrating a 4-micron sphere, and FIG. 2C is a picture illustrating a 8-micron sphere. FIG. 3A is a picture illustrating *Cryptosporidium*, FIG. 3B is a picture illustrating inorganic "dirt" and FIG. 3C is a picture illustrating *Giardia*. FIG. 4 is a picture illustrating *E. coli*. The white area is the brightest part of the image or most scattered photons. These images were taken with a 320 pixel by 240 pixel CMOS array camera. These images were not rotated to principle axis horizontal but were captured as the particle transited the laser beam. Each image has been normalized to intensity, otherwise the *E. coli* image would be the dimmest and the 8 micron sphere the brightest.

In some embodiments, the processing system 114 computes image symmetry for the captured picture (FIGS. 2, 3, and 4) to determine if it is, e.g., round or rod shape. This particle symmetry information can then be combined with the forward scattering amplitude to determine the particle classification without the need to, e.g., compare the image with images stored in a library.

Figure 5:
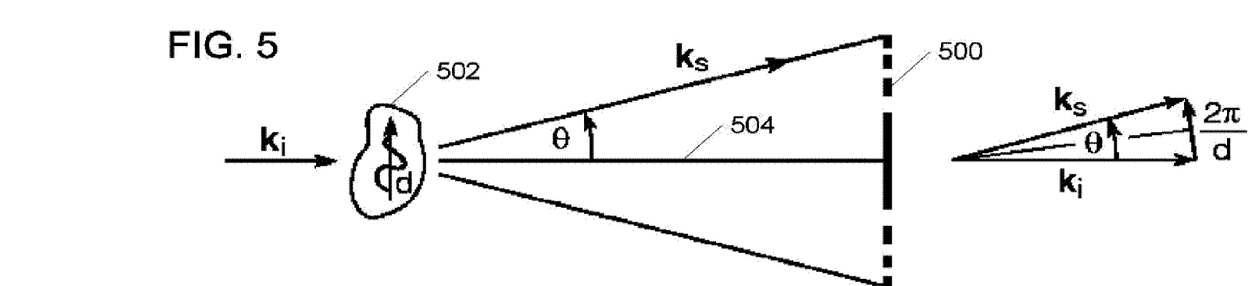
FIGS. 5-7 are diagrams illustrating a technique for using illumination incident at an angle in a light scattering detection system, such as the systems of FIGS. 1A and 1B.

As noted above, if some form of spherical lens, or other device, is not used, then only scattered light rays with an angle less the θ would be detected; however, if the illumination beam is incident at an angle, then light can be measured through twice the original measured scattering angles and still be captured by the detector. The ratio of the scattered light intensity from larger scattering angles to the smaller scattering angles approaches unity as the particle size decreases. Thus smaller particles scatter light into proportionately larger angles. Illuminating the sample at angle permits radiation scattered at large angles from smaller particles to still be captured by the by the detector's optical system thus, a greater resolution can be achieved. This is illustrated by FIGS. 5-7.

When illumination is incident upon a particle 502 along an optical axis 504, vector $k_i$ can be used to represent the illumination. As illumination incident along vector $k_i$ encounters particle 502, it will be scattered through a sphere of 360 degrees but only detected through a range of angles up to θ. Thus, a scattered light ray at the outer edge of the detector range can be represented by vector $k_s$.

Figure 6:
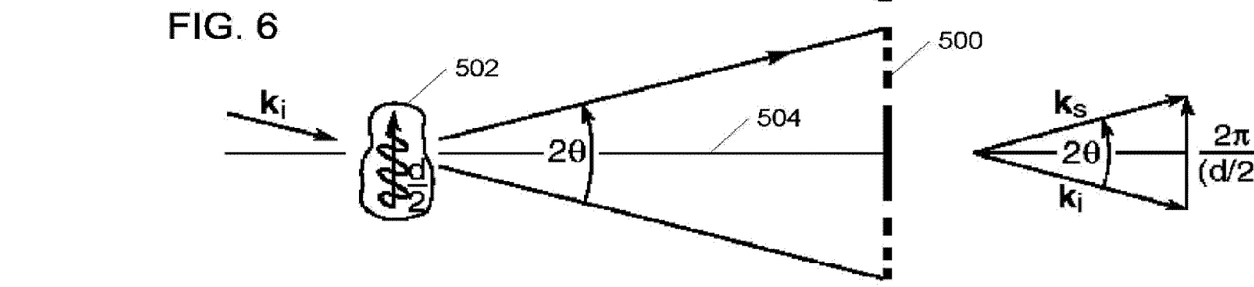

If, however, the illumination is incident at an angle illustrated by vector $k_i$ in FIG. 6, then the detector will be able to see light scattered through a greater angles. For example, the scattered light rays will be measured through an angle of 20. As a result, objective 500 can collect scattered light rays scattered through twice the angle as compared to the system in FIG. 5. Thus, the resolution of the system illustrated in FIG. 6 would be twice that of the system illustrated in FIG. 5.

Figure 7:
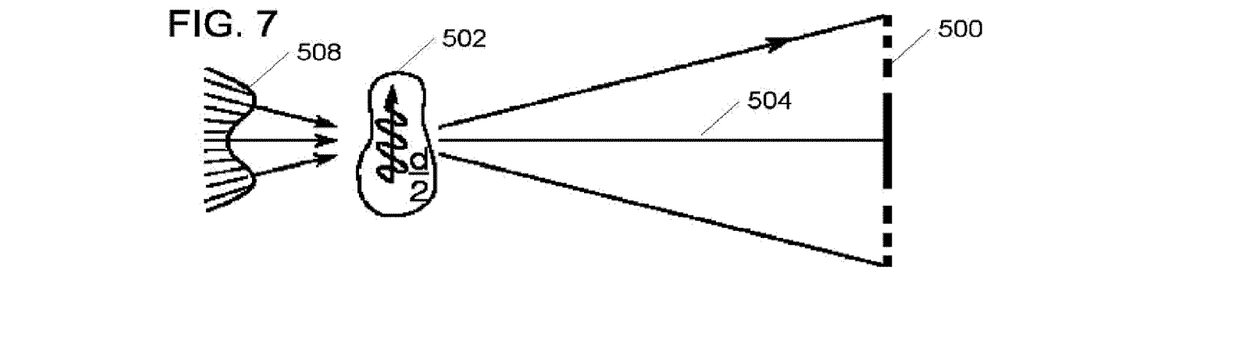

FIG. 7 is a diagram illustrating that the same effect can be achieved using a plurality of incident beams 508 that include beams incident at an angle from above and below the optical axis 504. Switching on or off the individual laser beams can provide additional multiple angles without having to provide additional detectors. If the switching is fast enough compared to the transit of the particle through the beam, then the additional angles can be obtained for the same particle.

It should be noted that objective 500 in FIGS. 5-7 can be a zone plate as well as another conventional optical element, including a holographic optical element.

Figure 8:
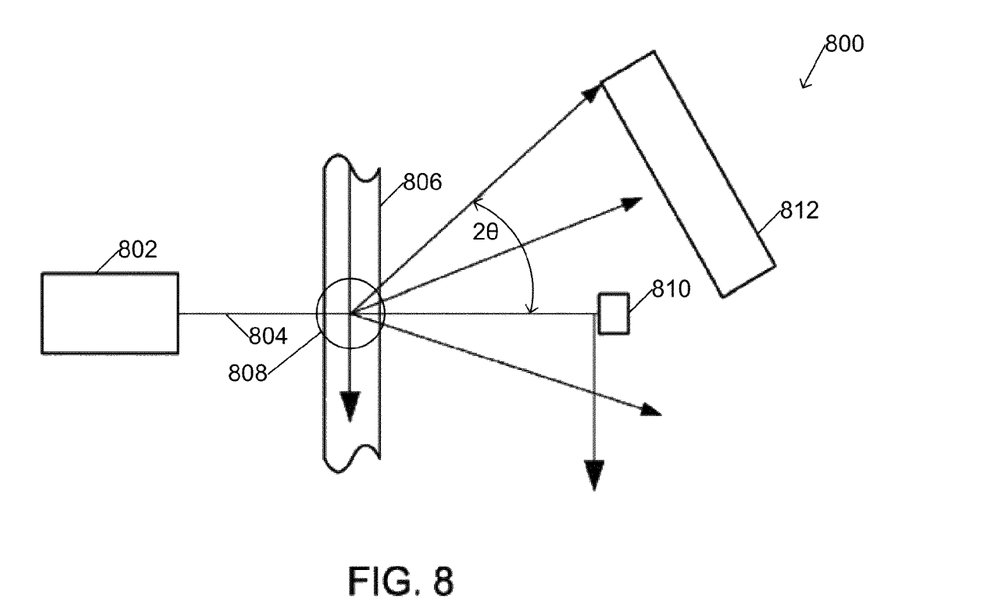
FIG. 8 is a diagram illustrating an example particle detection system that implements the technique of FIGS. 5-7 in accordance with one embodiment.
Figure 9:
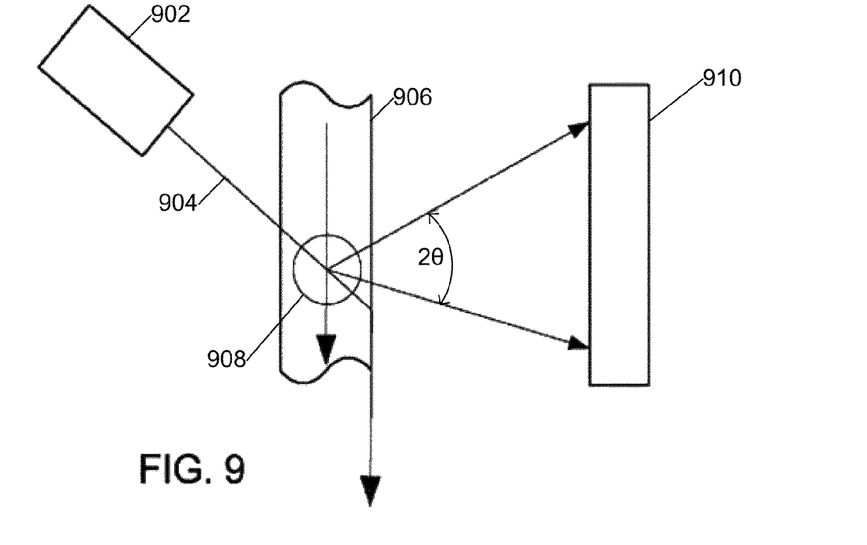
FIG. 9 is a diagram illustrating an example particle detection system that implements the technique of FIGS. 5-7 in accordance with another embodiment.

FIGS. 8 and 9 illustrate that the technique depicted in FIGS. 6 and 7 could be achieved by altering the position of the optical detector or by configuring the light source so that the illumination is incident at an angle upon the target zone. Thus, FIG. 8 is a diagram illustrating an example particle detection system 800 in which an optical detector 812 has been repositioned so as to capture scattered light rays scattered to an angle 20. In FIG. 8, a light source 802, such as a laser, produces a beam 804 that is incident on particles within target zone 808. It should be noted that a beam stop 810 can still be required within system 800 to deflect the beam traveling along the optical axis.

It will be understood that system 800 can comprise a processing system, but that such system is not illustrated for simplicity.

FIG. 9 is a diagram illustrating an example particle detection system 900 in which optical source 902 is configured such that beam 904 is incident upon target zone 908 at an angle equal to or greater than the critical angle defined by the phenomenon of total internal reflection. In the system of FIG. 900, by selecting the incident angle such that the beam experiences total internal reflection, beam 904 is internally reflected within flow cell 906, and thus a beam stop is not required. This can lower the cost and complexity of system 900 and can, therefore, be preferable.

Again, it will be understood that system 900 can comprise a processing system, but that such system is not illustrated for simplicity.

As mentioned above with respect to FIG. 1, angles larger than θ will be reflected internally within flow cell 106. In general, collecting high angle scattered light from an object in a liquid medium requires some mechanism to prevent the internal reflection of the high angles being sought. This problem can be referred to as Total Internal Reflection (TIR) of the high angle scattered light. TIR can occur at high to low indexes of refraction interfaces within the optics of the instrument, or system being used to observe or collect the scattered light, e.g., the interface between flow cell 106 and the external atmosphere.

In certain embodiments, a second surface curved mirror reflecting optic can be used to collect and reflect the light. Such an optic can allow easy capture of light angles up to 90° for all azimuthal angles, when the sample is index coupled with the non-reflecting surface of the collection optic. Such an optic can prevent TIR issues at angles greater than approximately 40°.

Figure 10:
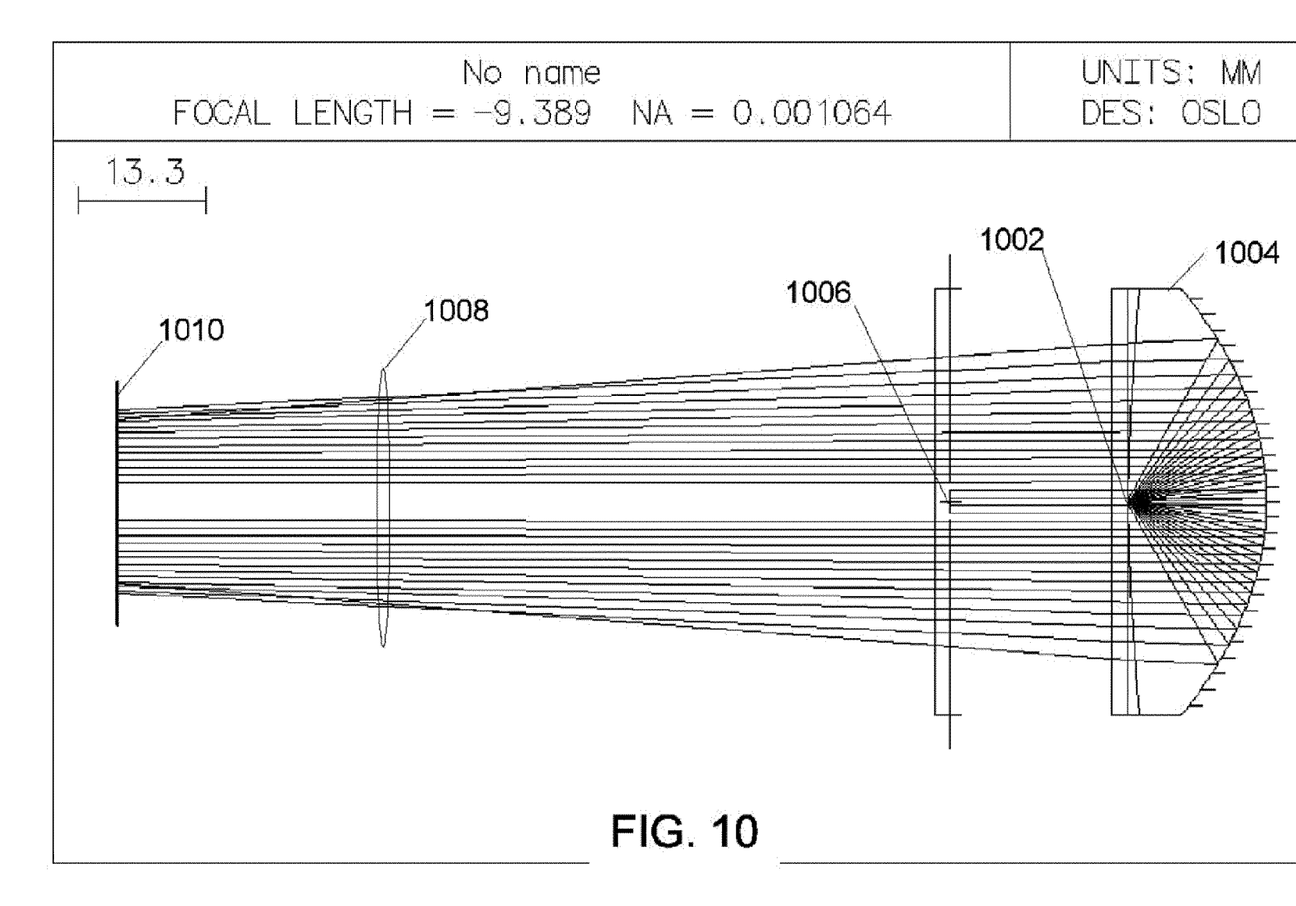
FIG. 10 is a diagram illustrating a spectrometer ray trace for light scattered by a particle suspended in a liquid medium and reflected by a curved mirror.

FIG. 10 is a diagram illustrating a scatterometer ray trace for light scattered by a particle 1002 and collected using a second surface curved mirror 1004. In the example of FIG. 10, light reflected through an angle of 60° by the reflective surface of mirror 1004 corresponds to light scattered through an angle of 90° by object 1002. The scattered light 1008 passes by beam stop 1006, which is configured to reflect the high intensity light traveling along the beam axis. Scattered light can then be incident on a detector surface 1010, such as a CCD.

Figure 11:
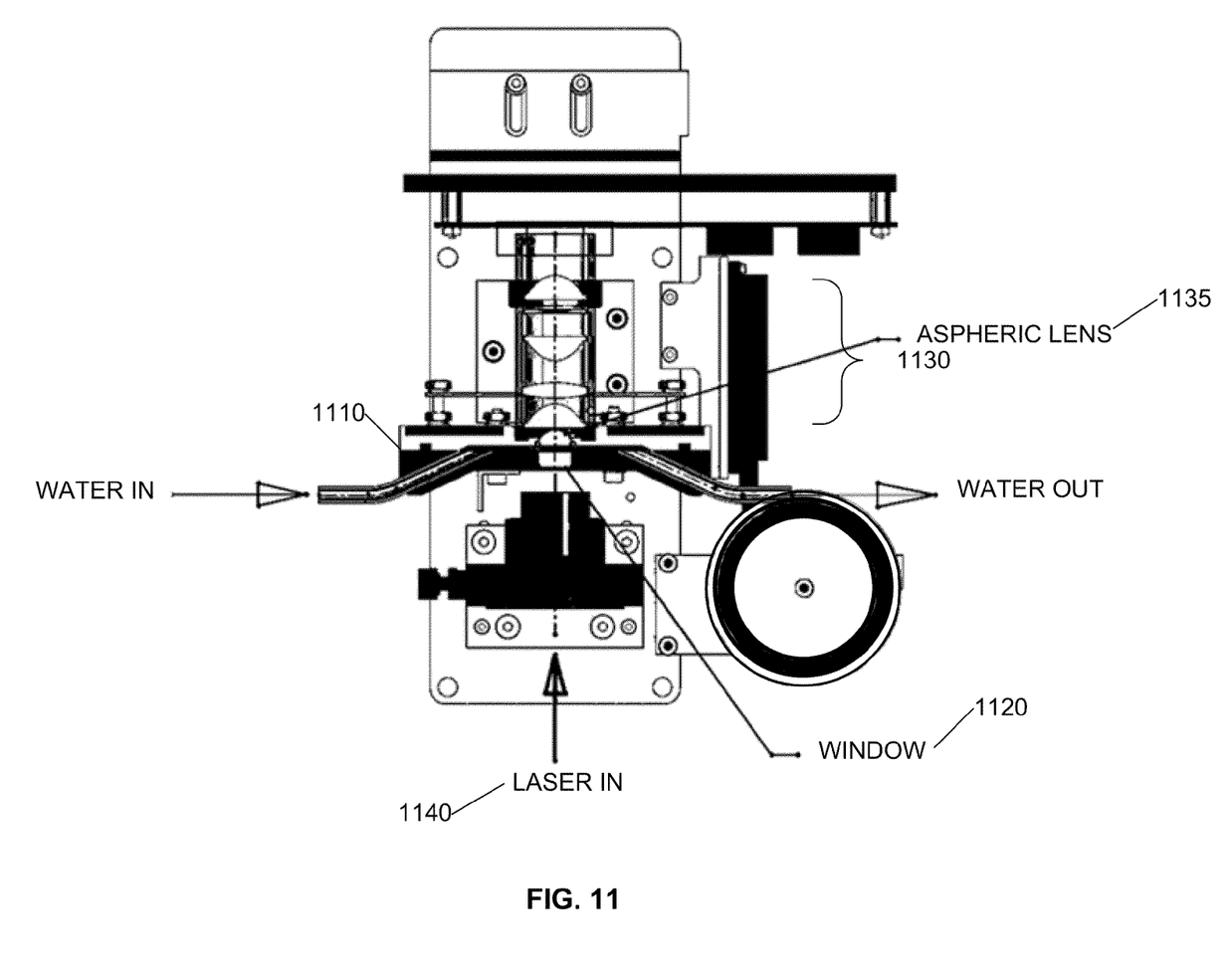
FIG. 11 is an assembly drawing for an implementation of a particle detection system configured in accordance with one embodiment.

FIG. 11 is an assembly drawing for an implementation of a particle detection system configured in accordance with one embodiment of the systems and methods described herein. As can be seen, the system 1100 includes a flow cell 1110 through which a fluid (e.g., water) enters and then exits. Flow cell 1110 is preferably made of a metal material. The flow cell 1110 includes a transparent, cylindrical window 1120 that has a horizontal width of about 15 mm. The width of the flow cell 1110 at the location of the window 1120 (e.g., where the window resides) can be from about 2 mm to 4 mm. A series of lenses 1130, beginning with an aspheric lens 1135 near the flow cell 1110 are configured to gather the scattered light rays from laser 1140, collimate them, and present them to the camera 142. In certain embodiments, the camera is a planar square array photodiode with resolution of 16×16 pixels, each pixel being~1 mm square and spaced at~1.5 mm. In the system 1100 depicted, the camera has about a 4 mm depth of focus that encompasses the portion of the flow cell 1110 through which the laser beam from laser 1140 travels.

Figure 12:
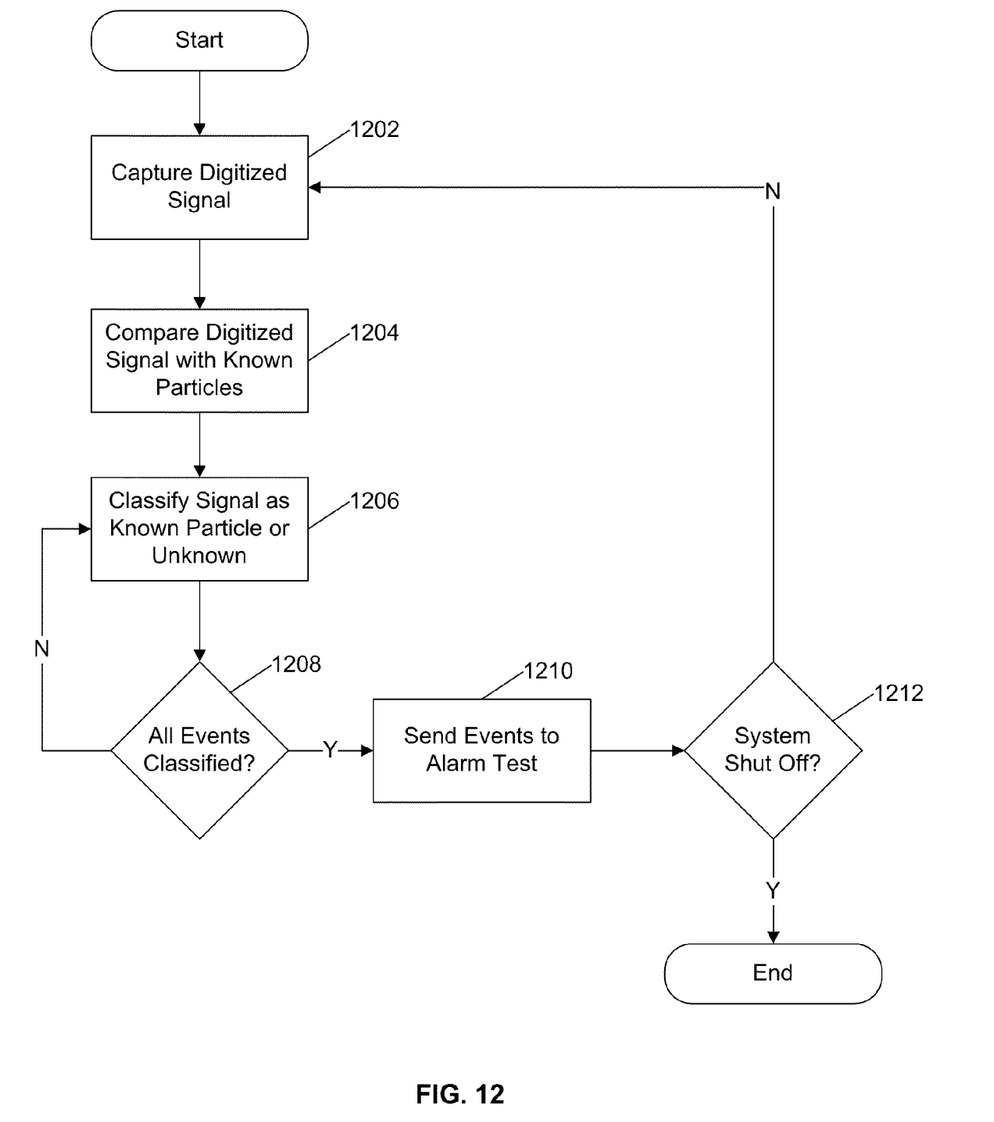
FIG. 12 is a flow chart illustrating an example method for operating system for classifying particle events in accordance with one embodiment.

FIG. 12 is a flow chart illustrating an example method for classifying particles in realtime in accordance with one embodiment. In step 1202, digitized signals from the detector elements, associated amplifiers, digitizing electronics, and digital signal conditioning in the camera are captured, e.g., from camera 112 of FIG. 1. The digitized signals include the forward scattering intensity (e.g., amplitude) of the incident scattered light and the picture of the scattered light rays. The digitized signals are then stored and processed 1204. One example method for processing the BioSignatures 13 described below with respect to FIG. 14. In step 1206, the particle of interest (e.g., represented by the digitized signals) is classified as one of the known particles or as an unknown particle. Classification of a known particle is based on having a correlation value above a predetermined threshold. For example, the size and shape of the particle and forward scattering intensity are used to determine which particle the digitized signals most closely match. This predetermined correlation value may be adjusted at any time. If, however, the digitized signals do not meet the correlation value for a known particle, the particle of interest is classified as unknown.

In step 1208, steps 1202 through 1206 can be repeated until all the digitized signals have been classified, generating a count of particles vs. species result. In step 1210, the classified results can be sent to the alarm test process illustrated in FIG. 13. In step 1212, steps 1202 through 1210 can be repeated until the system is shut off or the program is ended.

Figure 13:
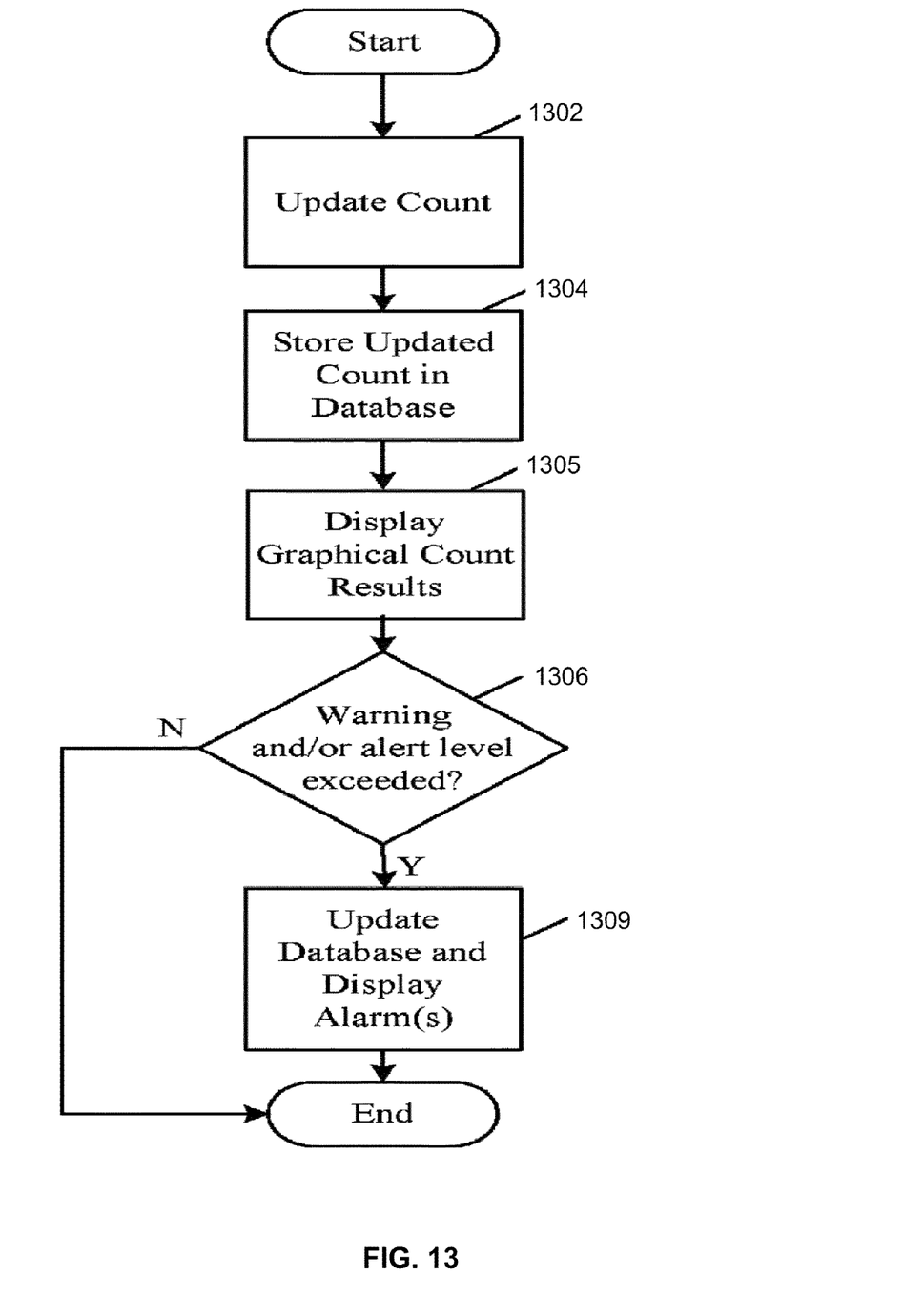
FIG. 13 is a flow chart illustrating example alarm and warning methods that can be implemented in a particle detection system in accordance with one embodiment.

FIG. 13 is a flow chart illustrating an example alarm and warning process in accordance with one embodiment. In step 1302, for each set of classified results and for each species within the results, the counts (e.g, number of particles) in each species are added to a species count vs. time record database within computer memory storage. In step 1304, the database receives the new count vs. species information and is updated. In step 1305, the count result can be displayed, e.g., via a graphical display. In step 1306, for each species, the results of step 1304 are examined to determine if the corresponding count rate exceeds certain warning levels or alert levels. In step 1309, if any warning or alert level is exceeded for any of the species or for the "unknowns" then a corresponding entry in the database can be created and the results displayed on a user graphical interface. Additionally, the warnings and alerts may be sent to external SCADA or computer systems used for operations monitoring. The system can be programmed to automatically divert the sample outflow from the target zone, which normally may go to a drain, to a sample bottle or to an external sample collecting filter for further analysis by the user.

Figure 14:
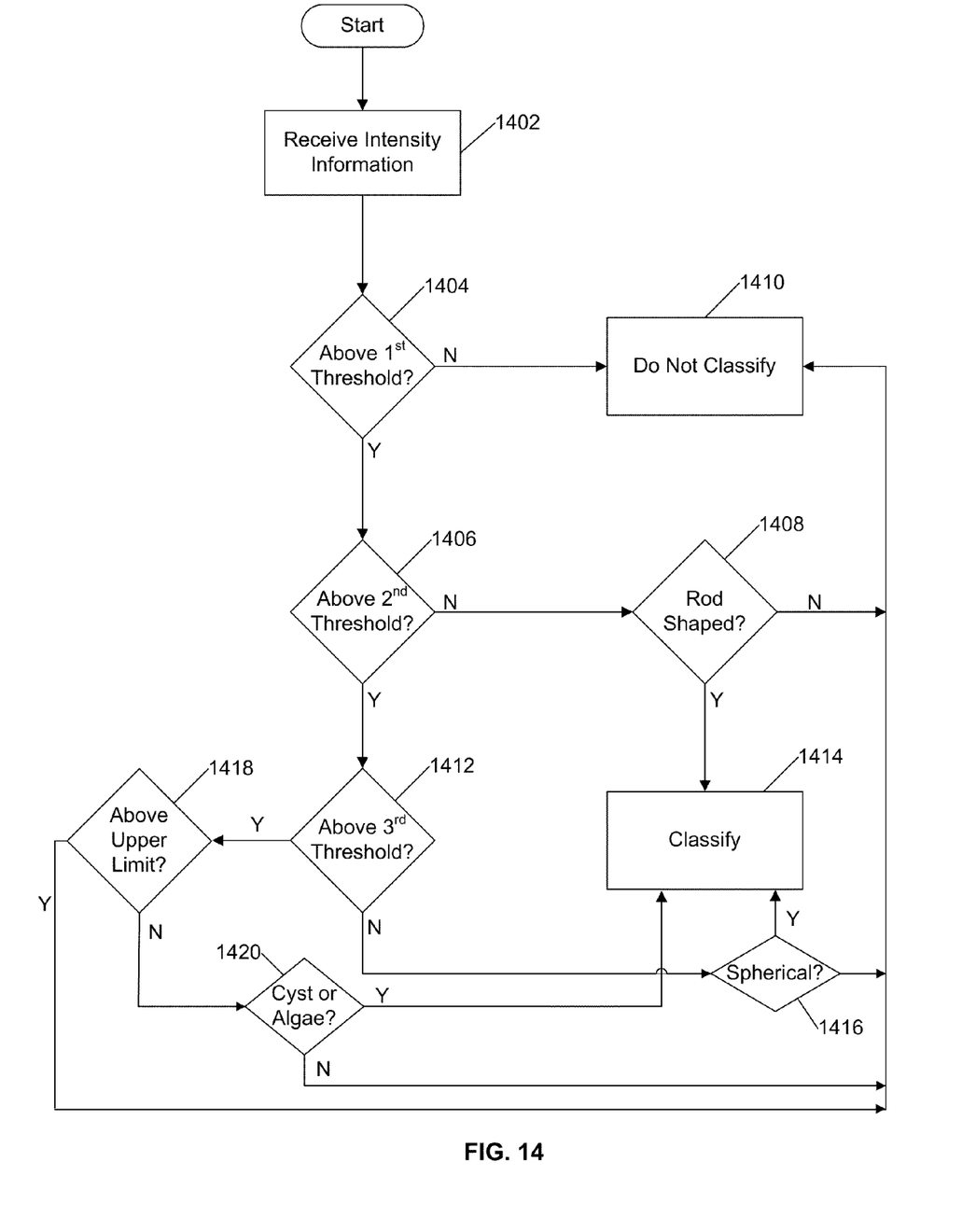
FIG. 14 is a flow chart illustrating an example method for processing BioSignatures in accordance with one embodiment.

FIG. 14 is a flow chart illustrating an example method for processing particles and obtaining classification of BioSignatures in accordance with one embodiment. As noted above, in certain embodiments, a set of thresholds can be used in combination with image information to classify particles detected in system 100. For example, the shape of the particle can be determined and used in conjunction with the forward intensity to quickly classify a particle.

Referring to FIG. 14, the particle information, e.g., forward intensity and picture information, can be received in step 1402. In step 1404, it can be determined whether the forward intensity is above a first threshold. If it is not, then the system can be configured so as to not classify the particle, or in certain embodiments to classify it as unknown. If the intensity is above the first threshold, then the system can be configured to determine if it is above a second threshold in step 1406.

If the forward intensity is above the first threshold, but not above the second threshold, then the system can determine the shape of the particle from the picture information in step 1412. For example, an image symmetry can be obtained and then used to classify the shape of the particle, e.g., as spherical or rod shaped. It will be understood that many particles of interest, e.g., as described above, have either spherical or rod shape. It will also be understood that each of these shape shapes a certain image symmetry, i.e., an axis about which the image, shape and intensity, is significantly spherical. The picture information and forward intensity information, can thus be use to determine an image symmetry. Image intensities and shapes can be stored, e.g., in system 100. Thus, by simply determining whether the intensity is in a certain range and the corresponding particle shape, a determination of the particle type can be made with a high degree of accuracy.

Accordingly, when it is determined that the intensity is within a range bound, e.g., by the first threshold and the second threshold and the particle has a certain shape, e.g., rod shaped, then the particle can be classified as rod-shaped, e.g. E-coli is a rod-shaped bacteria. If the image does not have any symmetry, or the wrong symmetry, then the particle can be unclassified or classified as unknown in step 1410.

If the intensity is below the second threshold as determined in step 1406, then the shape can be determined in step 1408 and if it is the correct shape, e.g., rod-shaped, then the particle can be classified at step 1414 as rod-shaped. If the shape is not correct, then the particle can go unclassified or classified as unknown in step 1410.

It will be understood that testing for third, fourth, etc., thresholds and corresponding shapes can also be performed as required by a particular implementation. For example, if the intensity level is above the second threshold, but below a third threshold as determined in step 1412, then the shape can be determined in step 1416, and if it is the correct shape, e.g., spherical, then the particle can be classified at step 1414. If the shape is not correct, then the particle can go unclassified or classified as unknown in step 1410.

It should also be understood that while true speciation does not necessarily occur in the example embodiment described above that speciation can still occur. In other words, while the system as described in the embodiment above determines shape and not specie, the shape and intensity can be correlated with a specie or group of species. For example, once it is known that a rod-shaped bacteria is present, then this can be correlated with at least the possibility that the bacteria present is *E. coli*, which is a rod shaped bacteria. Alternatively, the presence of a rod-shaped bacteria can be used to indicate that one of a plurality of rod-shaped bacteria, e.g., including *E. coli* is present.

In another embodiment, if the intensity level is above the third threshold, but below an upper limit as determined in step 1418, and if it is the correct shape, e.g., cyst or algae, then the particle can be classified at step 1414. If the shape is not correct or the intensity level is above the upper limit, then the particle can go unclassified or classified as unknown in step 1410. For example, if the particles are above the upper limit, they can be assumed to be mostly air bubbles. Additionally, in other embodiments, the order of thresholds can be reversed, e.g., the highest one can be tested for first.

Thus, by determining whether the intensity is in a certain range and the corresponding shape, a particle can be classified quickly and accurately, without the need to compare the BioSignature to known BioSignatures. This can also eliminate the need to store BioSignatures if desired.

Figure 15:
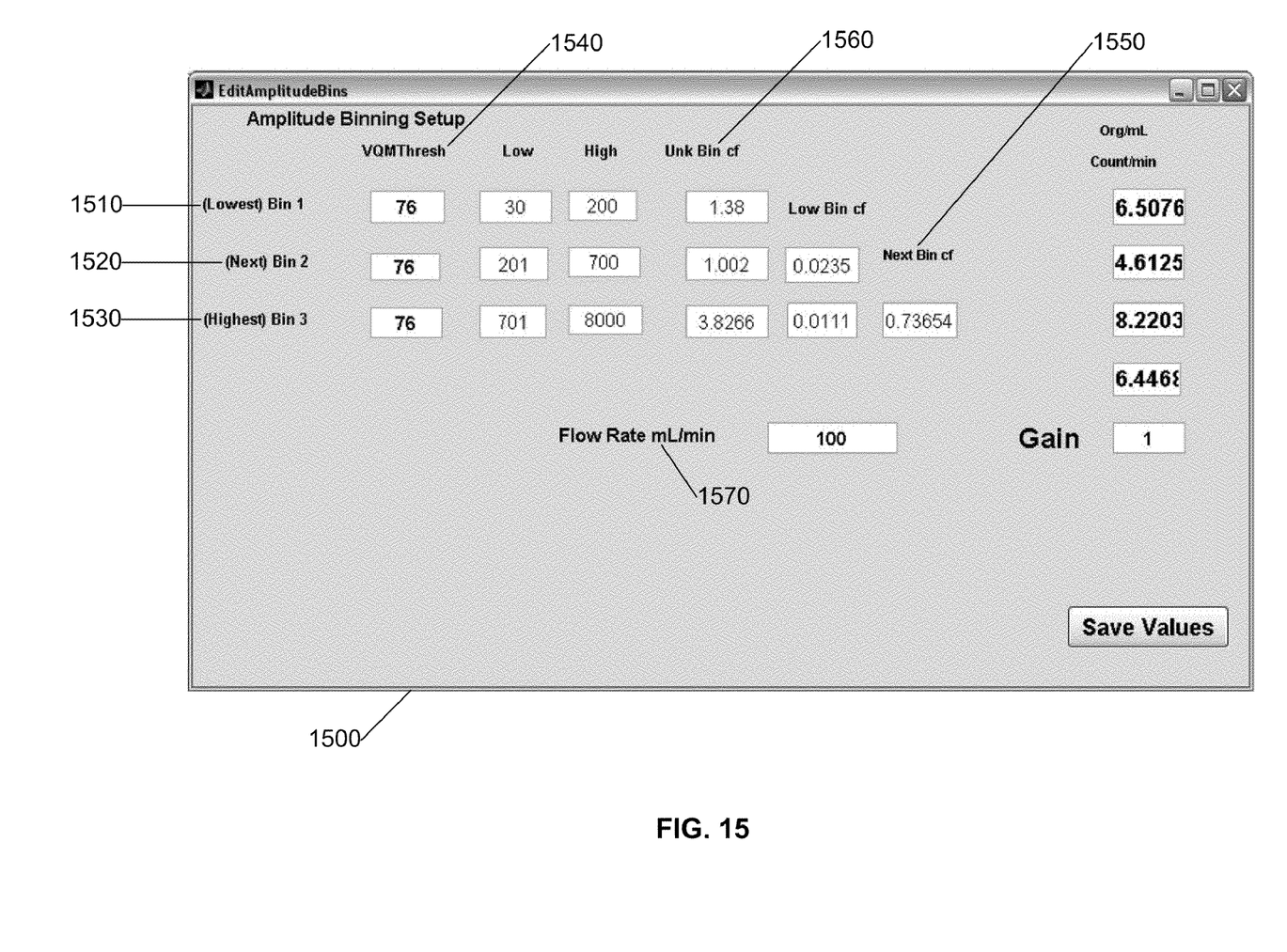
FIG. 15, an exemplary screen shot of threshold information used in the method for processing Biosignatures, as shown in FIG. 14.

For example, referring to FIG. 15, an exemplary screen shot 1500 of threshold information is shown. For example, in an embodiment, bin 1 (numeral 1510) corresponds to rods, bin 2 (numeral 1520) corresponds to spores, and bin 3 (numeral 1530) corresponds to protozoa cysts and algae. For an event to be classified, it has to fall in amplitude into one of the three bins; particles with values below the lowest and above the highest are not classified.

The VQMThresh column 1540 includes information relating to how well the shape corresponds to rods, small spheres, and large spheres respectively. If a particle or event scores lower than the VQMThresh value, the particle is classified as unknown.

The column 1550 to the far right (e.g., Next Bin cf) is for when the counts per minute are converted into concentration values. For example, in one embodiment, the Next Bin cf column 1550 value is the factor at which rod counts per minute are multiplied by to convert the rod count to organisms per milliliter (mL). For example, if there are 1000 counts per minute that fall into bin 1 (e.g., rods) and of those 42% of them have a VQMThresh greater than 76 for 420 counts per minute . . . and it is desired to have the value of organisms per mL . . . then multiply 42 by 6.5076 and get approximately 2,733 organisms per mL in the rod bin (e.g, bin 1). Thereafter, the column 1560 is used (e.g., unk Bin cf—or unknown bin correction factor), which has a value of 1.38 and the 1.38 is multiplied by the 420 counts per minute to get 580 counts per minute and used in subtracting from the left over counts per min in the rod bin 1000−420=580 counts per minute then minus the 580 counts calculated=0 counts per minute in the Unknowns. Then the 0 counts per minute in the unknowns are multiplied times 6.4468 to calculate the organisms per mL in the unknown channel. For perfect rods, there would be zero in unknowns. However, in reality there is typically counts per minute left over after this correction is performed. In some embodiments, if counts per minute are sufficient, then the correction factors do not need to be used.

The multiplication values 6.5076 and 6.4468 used in determining concentration were determined by physically inserting into particle free test water a known number of bacteria and or polystrene spheres to generate a known concentration of particles/mL and sending them through the detection system to generate counts per minute. Then, using the generated counts per minute and knowing what the initial concentration was, the organisms/mL factor can be calculated by taking the concentration and dividing by counts per minute; the organisms/mL factor has units of org/mL/counts per minute, so when it is multiplied by the counts per minute the resulting number is organisms per mL. For example, if water is tested with a known concentration of 10,000 particles per mL, which results in 1536 counts per minute classified into the spore channel, then we have 10,000/1536=6.51 factor.

It should be noted that counts per minute are proportional to flow rate (shown in column 1570). It should also be noted that the Gain value is normally 1, but for adjustments in amplitude, using the gain factor is better than adjusting the bin thresholds.

While the invention has been described with respect to a limited number of embodiments, the specific features of one embodiment should not be attributed to other embodiments of the invention. No single embodiment is representative of all aspects of the inventions. Moreover, variations and modifications therefrom exist. The invention has been described in terms of water as a liquid, however any substantially clear liquid may be the media to monitor for bacteria, such as process water used in manufacturing, sea water used for bathing, water that has added dissolved substances, such as sugars, alcohol, or other chemicals, or other liquids that may not have a water base, such as oils. Additional variations, for example, flowcells of different geometry can be used, light sources other then laser, such as LED, incandescent, mercury vapor, or multiple light sources, or multiple detectors can be used, and dedicated digital processors, other then common computers can be used to practice the present invention. In some embodiments, the devices are substantially free or essential free of any feature on specifically enumerated herein. Some embodiments of the method described herein consist of or consist essentially of the enumerated steps. The appended claims intend to cover all such variations and modifications as falling within the scope of the invention.

What is claimed:

1. A system for monitoring levels of particles in liquid, the system comprising:
    an optical axis;
    a target zone, the optical axis intersecting the target zone;
    at least one light source configured to generate a light beam and direct the light beam through the target zone;
    an optic lens system configured to collect light scattered by a particle associated with the particles in the liquid medium in the target zone and direct the scattered light to at least one detector, the detector configured to detect the forward intensity of the scattered light and generate an image of the particle; and
    a computer system coupled with the detector, the computer system configured to execute a set of programmed instructions to identify and classify the particle, the instructions causing the computer system to:
        determine whether the forward intensity of the scattered light is within a pre-determined range,
        when it is determined that the intensity is within the pre-determined range, then determine a shape associated with the particle based on the image of the particle, and
        assign a classification type to the particle based on the forward intensity and the shape.

2. The system of claim 1, wherein determining the shape comprises determining a symmetry for the particle.

3. The system of claim 2, wherein the symmetry is round or spherical.

4. The system of claim 1, wherein determining whether the forward intensity is within a pre-determined range comprises determining whether the forward intensity is above or below a first threshold.

5. The system of claim 4, wherein the instructions cause the computer to further determine whether the forward intensity is within a second predetermined range when it is determined that the forward intensity is not within the pre-determined range.

6. The system of claim 5, wherein determining whether the forward intensity is within the second pre-determined range comprises determining whether the forward intensity is above or below a second threshold.

7. The system of claim 1, wherein the instructions cause the computer to further:
    calculate a plurality of count rates for the classification type,
    store the plurality of count rates,
    calculate a trend in the stored plurality of count rates, and
    generate an alarm if the trend is undesirable.

8. The system of claim 1, wherein the particle is a bacteria.

9. The system of claim 8, wherein the bacteria are a Heterotropic Plate Count (HPC) bacteria.

10. The system of claim 8, wherein the bacteria are an indicator of biofilm slough-off, growth of a biofilm, or both.

11. The system of claim 1, wherein the liquid is a brine reject produced by a Reverse Osmosis RO process.

12. The system of claim 1, wherein the liquid is an inlet feed water for a RO process.

13. The system of claim 1, wherein the liquid is a RO product of a RO process.

14. The system of claim 1, wherein the liquid is at least one of a brine reject produced by a Reverse Osmosis RO process, an inlet feed water for a RO process, or a RO product of a RO process.

15. In a system comprising a multi-angle light scattering device, a detector configured to detect scattered light from a particle generated by the multi-angle light scattering device and to generate forward intensity information and an image of the particle, and a computer system coupled with the detector, a method of monitoring liquid for normal micro-organism levels comprising:

monitoring a liquid with the multi-angle light scattering device;

generating forward intensity information and image information when a particle is detected in the liquid;

in the computer, determining whether the forward intensity of the scattered light is within a pre-determined range, when it is determined that the intensity is within the pre-determined range, then determining a shape associated with the particle based on the image of the particle, and assigning a classification type to the particle based on the forward intensity and the shape.

16. The method of claim 15, wherein determining the shape comprises determining a symmetry for the particle.

17. The method of claim 16, wherein the symmetry is round or spherical.

18. The method of claim 15, wherein determining whether the forward intensity is within a pre-determined range comprises determining whether the forward intensity is above or below a first threshold.

19. The method of claim 18, further comprising determining whether the forward intensity is within a second predetermined range when it is determined that the forward intensity is not within the pre-determined range.

20. The method of claim 19, wherein determining whether the forward intensity is within the second pre-determined range comprises determining whether the forward intensity is above or below a second threshold.

21. The method of claim 15, further comprising:

in the computer, generating a plurality of count rates for classes of particles associated with target micro-organisms;

in the computer, generating a trend analysis for the target micro-organisms based on the count rates; and in the computer, generating an alarm if the trend analysis indicates an undesirable change in the normal count rate for the target micro-organism.

22. The method of claim 15, wherein the monitored liquid is Reverse Osmosis Brine reject water.

23. The method of claim 15, wherein the liquid is a brine reject produced by a Reverse Osmosis RO process.

24. The method of claim 15, wherein the liquid is an inlet feed water for a RO process.

25. The method of claim 15, wherein the liquid is a RO product of a RO process.

26. The method of claim 15, wherein the liquid is at least one of a brine reject produced by a Reverse Osmosis RO process, an inlet feed water for a RO process, or the RO product of a RO process.

27. The method of claim 15, wherein the trend is undesirable if the count rates fall below a threshold for a determined period of time.

* * * * *